United States Patent

Matoba et al.

[11] Patent Number: 5,993,209
[45] Date of Patent: Nov. 30, 1999

[54] PERIODONTAL POCKET MEASUREMENT APPARATUS

[75] Inventors: Kazunari Matoba; Hirofumi Jikuhara; Hiroaki Kusakabe, all of Kyoto, Japan

[73] Assignee: Kabushiki Kaisha Morita Seisakusho, Kyoto, Japan

[21] Appl. No.: 08/987,330

[22] Filed: Dec. 9, 1997

[30] Foreign Application Priority Data

Dec. 12, 1996 [JP] Japan .................................. 8-352680
Dec. 16, 1996 [JP] Japan .................................. 8-353635

[51] Int. Cl.$^6$ .................................................. A61C 19/04
[52] U.S. Cl. ................................ 433/72; 600/589; 33/514
[58] Field of Search ....................... 433/72, 75; 600/589; 33/514

[56] References Cited

U.S. PATENT DOCUMENTS

| | | |
|---|---|---|
| 3,058,225 | 10/1962 | Ward . |
| 3,330,040 | 7/1967 | Kahn ........................................ 433/72 |
| 3,559,292 | 2/1971 | Weissman ................................. 433/72 |
| 3,943,914 | 3/1976 | Grenfell et al. ......................... 600/589 |
| 4,677,756 | 7/1987 | Simon et al. . |
| 4,764,114 | 8/1988 | Jeffcoat et al. ........................ 433/72 |
| 4,904,184 | 2/1990 | Murphy et al. ........................ 433/72 |
| 4,960,132 | 10/1990 | Habekost ............................... 433/72 |
| 4,979,898 | 12/1990 | Rand ..................................... 433/72 |
| 4,995,403 | 2/1991 | Beckman et al. ..................... 433/72 |
| 5,144,753 | 9/1992 | Murphy ................................. 433/72 |
| 5,318,442 | 6/1994 | Jeffcoat et al. ....................... 433/72 |
| 5,460,522 | 10/1995 | Scarffe ................................. 433/72 |

FOREIGN PATENT DOCUMENTS

| | | | |
|---|---|---|---|
| 286067 | 10/1988 | European Pat. Off. ............... 433/72 |
| WO 89/05117 | 6/1989 | WIPO ................................. 433/72 |

*Primary Examiner*—Ralph A. Lewis
*Attorney, Agent, or Firm*—Koda & Androlia

[57] ABSTRACT

The periodontal pocket measurement apparatus of the present invention comprises a main handpiece unit provided with a cover member for covering the front end portion thereof, an operation member mounted at the front end of the cover member and being slidable in the longitudinal direction of the cover member, a flexible sleeve attached to the operation member and projecting from the front end of the cover member, and a probe attached to the cover member, passing through the sleeve and being exposable at its tip from the tip of the sleeve, being characterized in that the main handpiece unit is provided with energizing means for pushing a movable portion including the operation member and the sleeve toward the front end. With this structure, operation can be made easily when measuring the depth of a periodontal pocket of a patient by detecting the positional difference between the tip of the probe and the tip of the sleeve when the tip of the probe is inserted into the bottom portion of the periodontal pocket and the tip of the sleeve is made contact with the upper fringe of the gingiva.

24 Claims, 11 Drawing Sheets

|  | | | | | | | | | | |
|---|---|---|---|---|---|---|---|---|---|---|
| | Plaque chart | ✕ | ✕ | ✕ | ✕ | ✕ | ✕ | ✕ | ✕ | ✕ |
| | Others | | | | | | | | | |
| Upper jaw | Mobility | | | | | | | | | |
| | Pocket depth — Buccal side | | | | | | | | | |
| | Pocket depth — Palatal side | | | | | | | | | |
| | | 8 | 7 | 6 | 5 | 4 | 3 | 2 | 1 | 1 |
| | Pocket depth — Lingual side | | | | | | | | | |
| | Pocket depth — Buccal side | | | | | | | | | |
| Lower jaw | Mobility | | | | | | | | | |
| | Others | | | | | | | | | |
| | Plaque chart | ✕ | ✕ | ✕ | ✕ | ✕ | ✕ | ✕ | ✕ | ✕ |

FIG. 11A

| Mobility | | | | | | | | | | | | | | | |
|---|---|---|---|---|---|---|---|---|---|---|---|---|---|---|---|
| Epp (mm) | | | | | | | | | | | | | | | |
| | 8 | 7 | 6 | 5 | 4 | 3 | 2 | 1 | 1 | 2 | 3 | 4 | 5 | 6 | 7 | 8 |
| Epp (mm) | | | | | | | | | | | | | | | |
| Mobility | | | | | | | | | | | | | | | |

FIG. 11B

PERIODONTAL POCKET MEASUREMENT APPARATUS

BACKGROUND OF THE INVENTION

1. Field of the Invention

The present invention relates to a periodontal pocket measurement apparatus for use in dental diagnosis.

2. Description of the Prior Art

Measuring the depth of a periodontal pocket caused by a periodontal disease, is one of important diagnostic activities in dental diagnosis. Known apparatuses for the measurement comprise a probe at the tip of a handpiece and a sleeve for covering the probe, wherein the probe and the sleeve are made slidable relatively to each other, being characterized in that the depth of a periodontal pocket can be detected by measuring the positional difference between the tip of the probe and the tip of the sleeve when the tip of the probe is made contact with the bottom portion of the periodontal pocket and the tip of the sleeve is made contact with the upper fringe of a gingiva (see Japanese Utility Model Publication 53-14069, Japanese Patent Publication 62-24098 and Utility Model Publication 62-32018, for example).

However, in these conventional apparatuses, since the direction of the probe is fixed with respect to the main handpiece unit, it is difficult to operate the probe. Furthermore, the portion of the handpiece to be inserted into the mouth of a patient cannot be easily subjected to sterilization by autoclave. Moreover, the mechanism is generally complicated and large, and it is high in cost.

In addition, various apparatuses have been proposed as apparatuses for recording examination results and outputting the results as necessary (see Japanese Laid-open Patent Application 59-40102, for example). However, such apparatuses cannot output diagnosis results in accordance with predetermined formats, and much time is required for clerical work incident to diagnosis, such as data processing.

SUMMARY OF THE INVENTION

Accordingly, a first object of the present invention is to provide a sanitary apparatus which can be easily operated and sterilized, and a second object of the present invention is to rationalize clerical work incident to diagnosis by using the apparatus.

In order to attain the above-mentioned objects, the periodontal pocket measurement apparatus of the present invention comprises a main handpiece unit provided with a cover member for covering the front end portion thereof, an operation member mounted at the front end of the cover member and being slidable in the longitudinal direction of the cover member, a flexible sleeve attached to the operation member and projecting from the front end of the cover member, and a probe attached to the cover member, passing through the sleeve and being exposable at its tip from the tip of the sleeve, being characterized in that the main handpiece unit is provided with energizing means for pushing a movable portion including the operation member and the sleeve toward the front end.

The above-mentioned energizing means has a pushing member, and can have a structure wherein the movable portion is energized toward the front end by contacting the pushing member with the movable portion. In addition, limiting means is provided to stop the movement of the movable portion at the position where the tip of the sleeve aligns or nearly aligns with the tip of the probe. The limiting means is provided in the main handpiece unit and structured to limit the movement of the pushing member in the front end direction at a predetermined position. With this structure, operation can be made easy when measuring the depth of a periodontal pocket of a patient by detecting the positional difference between the tip of the probe and the tip of the sleeve when the tip of the probe is inserted into the bottom portion of a periodontal pocket and the tip of the sleeve is made contact with the upper fringe of a gigiva.

In addition, the periodontal pocket measurement apparatus of the present invention further comprises a stationary portion provided in the main handpiece unit, a traveling portion connected to the pushing member of the energizing means and moving together with the pushing member, and a sensor for detecting the displacement of the traveling portion with respect to the stationary portion and for outputting a detecting signal corresponding to the movement distance of the sleeve. With this structure, it is possible to output the measurement results of the depth of the periodontal pocket as electrical signals.

The cover member is structured so as to be rotatable together with the sleeve and the probe with respect to the longitudinal axis of the main handpiece unit, or structured so as to be removable from the main handpiece unit. With this structure, the probe can be pointed in a desired direction depending on the direction of a tooth, and periodontal pocket measurement can thus be conducted easily. Furthermore, the cover member for covering the front end portion of the main handpiece unit and other members can be removed and sterilized. In particular, by using the cover member, probe and operation member made of heat-resistant materials, sterilization by autoclave can be carried out at high temperature, whereby it is possible to obtain a safe and sanitary apparatus.

Furthermore, the main handpiece unit is provided with a measurement circuit having a function capable of calculating the movement distance of the tip of the sleeve depending on the output from the sensor. With this structure, the handpiece can be made cordless, whereby its operability can be improved. Moreover, the measurement circuit can be installed in a control unit provided separately from the main handpiece unit, whereby the weight of the handpiece can be easily reduced.

In particular, by using the separately provided control unit, the calculation results obtained by the measurement circuit can be easily output in accordance with predetermined formats indicating the tooth numbers of teeth to be measured and the depth of a periodontal pocket at each measurement position, and a function for communicating with external devices can also be easily provided. Consequently, effort for clerical work, such as data processing, can be reduced, and a variety of applications are made possible by using a large capacity control unit.

Actual structures of the periodontal pocket measurement apparatus of the present invention will be made clarified by the following descriptions on an embodiment thereof.

BRIEF DESCRIPTION OF THE DRAWINGS

FIG. 11A shows an example of a format of an examination result table used for the control unit;

FIG. 11B shows another example of a format of an examination result table used for the control unit;

DETAILED DESCRIPTION OF THE PREFERRED EMBODIMENTS

Figure 1:
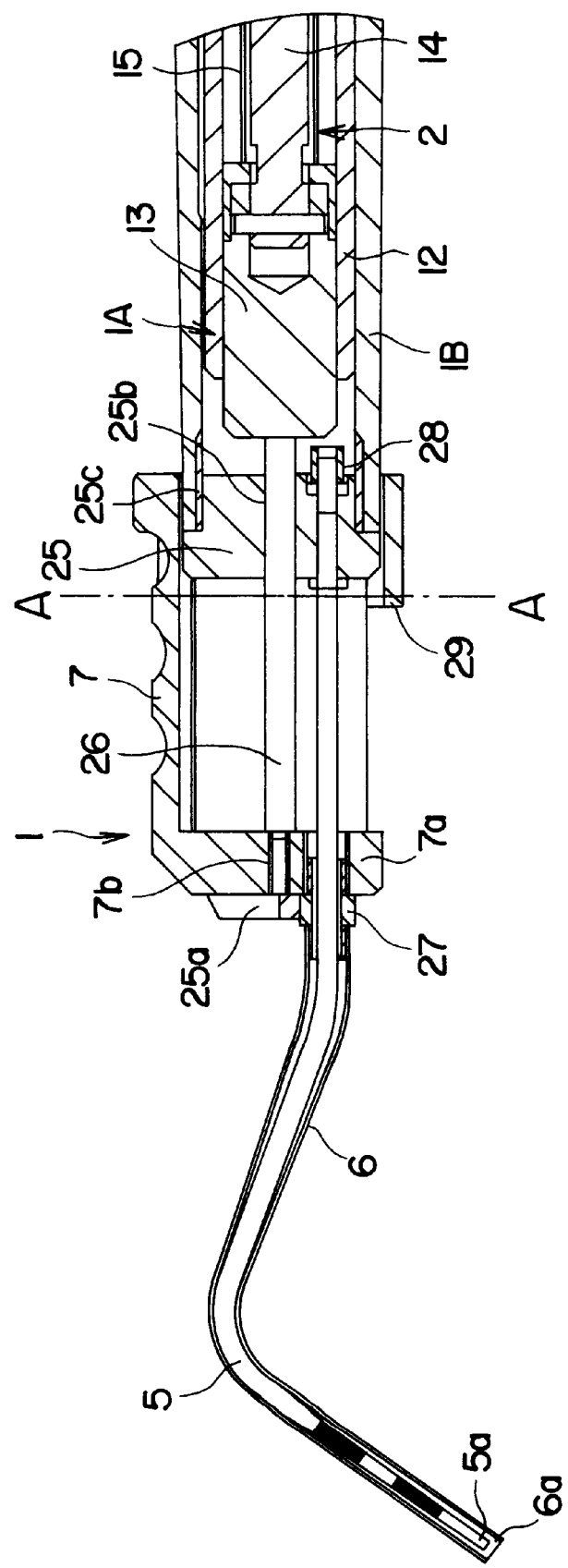
FIG. 1 is a magnified sectional view showing the front end portion of a handpiece in accordance with an embodiment of the present invention.

Next, an embodiment in accordance with the present invention will be described below. In the present specification, the left side and the right side in FIGS. 1 to 4 are referred to as "front side" and "rear side," respectively, and terms, such as front end and rear end, are used accordingly.

Referring to the figures, reference code 1 represents a pencil-shaped handpiece comprising a main handpiece unit 1A and a cover member 1B for covering the front end portion of the main handpiece unit 1A. Reference code 2 represents energizing means, and reference code 3 represents a sensor. These are built in the main handpiece unit 1A. A cord 4 for connection to a control unit (not shown) is installed at the rear end of the main handpiece unit 1A. In addition, reference code 5 represents a probe, reference code 6 represents a sleeve, and reference code 7 represents an operation member. These are attached to the cover member 1B. The main handpiece unit 1A has a structure wherein a pipe-shaped member 12 is secured to the front end of a base portion 11 in which the cord 4 is installed. The pipe-shaped member 12 covers the entire circumference on the front end side of the base portion 11, and projects forward.

Although the sectional shapes of the inner and outer surfaces of the cover member 1B are circular as shown in the figures, the shapes may have a partially chipped noncircular shape, such as a C-like or U-like shape, or a noncircular shape, such as a polygonal or oval shape.

Reference code 11a represents a threaded portion for integrating the pipe-shaped member 12 with the base portion 11 by screw engagement. The diameter of the pipe-shaped member 12 is made smaller ahead of the threaded portion 11a. A piston-shaped slider 13 is slidably inserted into the small diameter portion. The traveling portion 3a of the sensor 3 is connected to the slider 13 via a connecting rod 14. A coil spring 15 is disposed between the front end surface of the base portion 11 and the rear end surface of the slider 13 in a compressed condition. By the combination of these members, the energizing means 2 is formed to energize the slider 13 in the front end direction. Furthermore, the front fringe 3b of the traveling portion 3a of the sensor 3 makes contact with a stepped portion 12b formed on the inner surface of the base portion 11. This structure provides limiting means 2a which prevents the traveling portion 3a, that is, the slider 13, from moving further in the front end direction.

Figure 7:
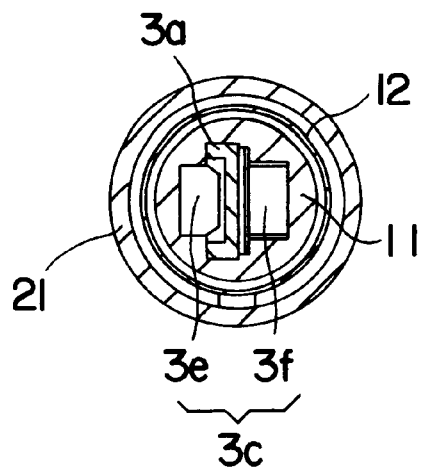
FIG. 7 is a sectional view taken on line B—B of FIG. 2.

The sensor 3 comprises the traveling portion 3a and a stationary portion 3c secured to the base portion 11. The traveling portion 3a has a shape of a slim frame provided with a light-transmission window 3d inside. On the window 3d, lightproof calibration markings (not shown) are provided at constant intervals in the longitudinal direction. Furthermore, a photocoupler comprising an LED 3e and a phototransistor 3f is used at the stationary portion 3c. The traveling portion 3a is disposed between the LED 3e and the phototransistor 3f (see FIG. 7). Accordingly, when the traveling portion 3a moves with respect to the stationary portion 3c, incident light from the LED 3e to the phototransistor 3f is interrupted by the calibration markings. By counting the number of interruption times, the movement distance of the traveling portion 3a can be optically detected in a noncontact condition. A measurement circuit for this detection is described later. The sensor 3 is electrically connected to the control unit (not shown) via the cord 4, but the lead wires inside the base portion 11 are not shown.

Figure 4:
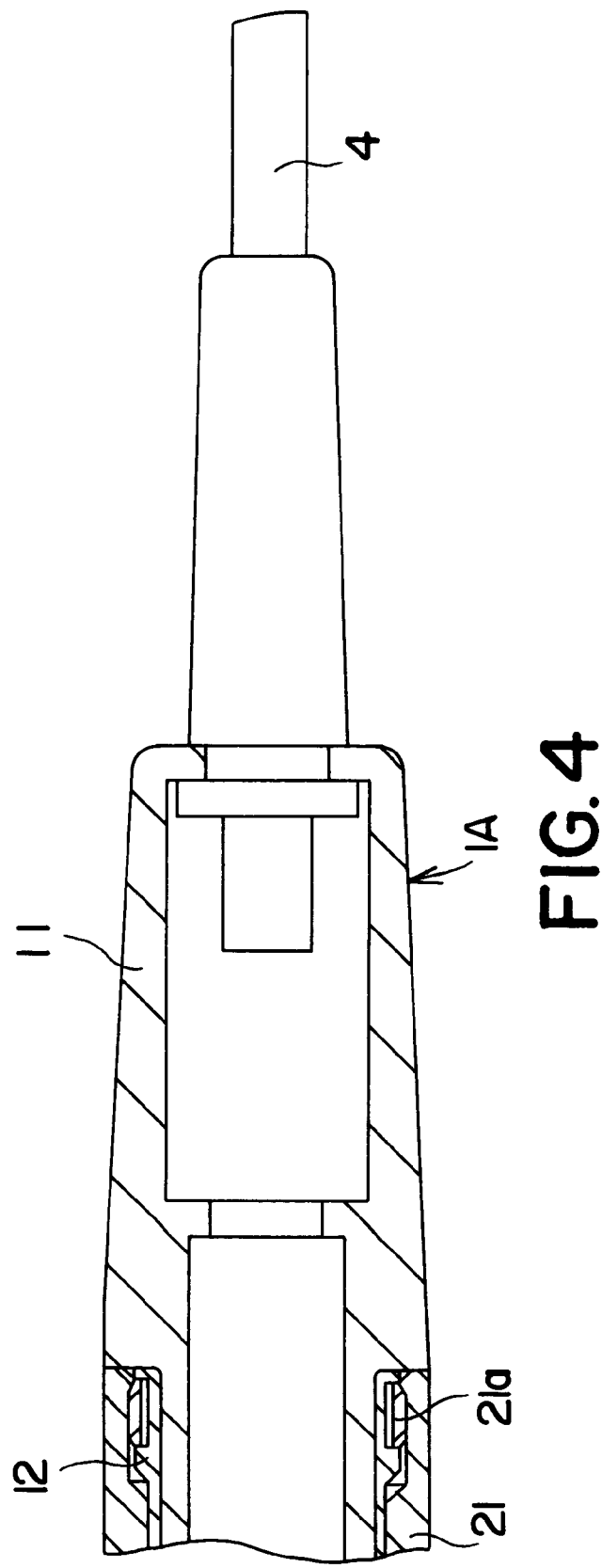
FIG. 4 is a magnified sectional view showing the rear end portion of the handpiece.

A C-ring 21a and a C-ring catch 21 are installed on the outer surface of the rear end of the pipe-shaped member 12 (see FIG. 4). The cover member 1B is secured to the front end side of the C-ring catch 21 via the threaded portion 21b. The inner surfaces of the C-ring catch 21 and the cover member 1B are pipe-shaped so as to match the outer surface of the pipe-shaped member 12 of the main handpiece unit 1A. The pipe-shaped member 12 is completely covered with the C-ring catch 21 and the cover member 1B. Since the C-ring catch 21 is just engaged with the base portion 11 via the C-ring 21a, the cover member 1B is rotatable together with the C-ring catch 21 with respect to the base portion 11, and can be removed from the base portion 11 by simple operation.

Reference code 25 represents a cap having a frame 25a shaped to enclose the front surface thereof. Reference code 26 represents a push bar, reference code 27 represents a sleeve catch, reference code 28 represents a probe holder, and reference code 29 represents a ring-shaped operation portion. The operation member 7 is a nearly L-shaped member integrated with a front plate 7a. A space is provided inside the frame 25a so that the front plate 7a can be inserted and moved therein. The operation member 7 is integrated with the cap 25 by disposing the front plate 7a inside the frame 25a, by passing the push bar 26 through a hole 25b provided in the cap 25 from behind and by screwing the push bar 26 into the threaded portion 7b of the front plate 7a disposed in the space inside the frame 25a. Furthermore, the operation member 7 is installed on the cover member 1B together with the cap 25 by screwing the threaded portion 25c of the cap 25 into the front end of the cover member 1B.

The probe 5 tapers down toward its tip and is bent in the middle as shown in the figures. The sleeve catch 27 is pipe-shaped so as to allow the probe 5 to pass through, and attached to the front plate 7a. The probe 5 is installed at the front end of the cover member 1B by inserting the base portion of the probe 5 into the sleeve catch 27 from the front side and by further inserting the probe 5 into the probe holder 28 provided in the cap 25. The sleeve 6 is formed of closely-wound thin metal wire made of stainless steel or the like and thus flexible. The wire winding diameter at the tip of the sleeve 6 is reduced in accordance with the shape of the probe 5. The sleeve 6 is attached to the operation member 7 by inserting the base portion of the sleeve 6 covering the probe 5 into the support port of the sleeve catch 27.

Figure 5:
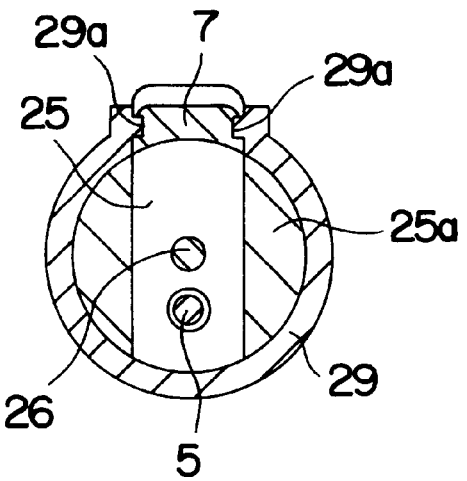
FIG. 5 is a sectional view taken on line A—A of FIG. 1.
Figure 6:
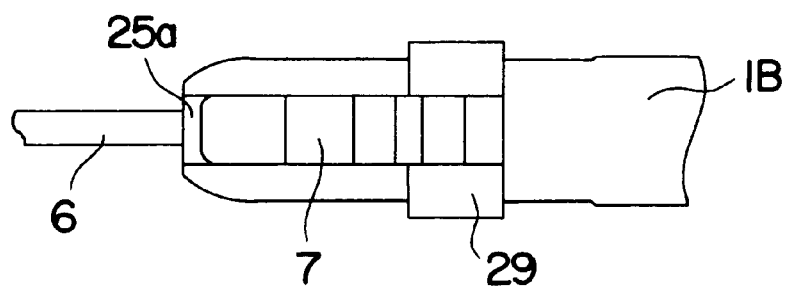
FIG. 6 is a plan view showing the front end portion of the handpiece.

In addition, the ring-shaped operation portion 29 encloses the tip portion of the cover member 1B and the cap 25, and is made of an elastic material. Furthermore, the ring-shaped operation portion 29 is removably engaged with the operation member 7 via concave and convex portions 29a formed between both ends of the operation portion 29 and the side fringes of the operation member 7 (see FIG. 5).

The cover member 1B, the operation member 7, the cap 25 and the ring-shaped operation portion 29, which are to be sterilized, are made of heat-resistant materials so that they can be removed together with the probe 5 and the sleeve 6 from the base portion 11 and sterilized by autoclave as described later.

Figure 2:
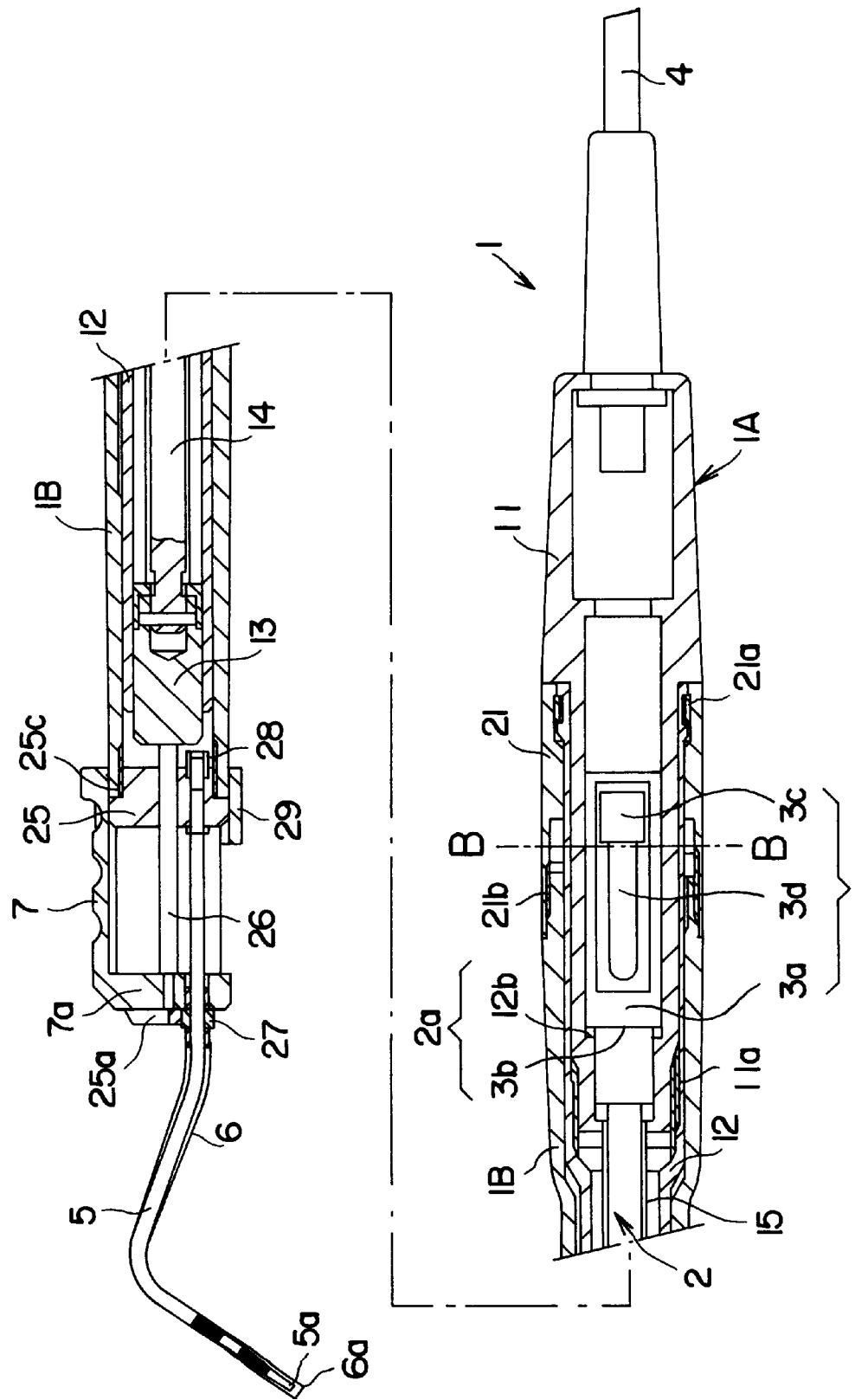
FIG. 2 is an overall sectional view showing the handpiece.

FIG. 2 shows a standby condition of the handpiece comprising all the members having been assembled as described above. More specifically, the slider 13 acts as a pushing member for the energizing means 2. By the energizing force of the coil spring 15, the slider 13 makes contact with the push bar 26 and pushes the push bar 26 forward. The operation member 7, which is movable back and forth inside the frame 25a of the cap 25, has been moved forward by the pushing force to the position wherein the front plate 7a makes contact with the frame 25a which prevents further movement. The lengths of the probe 5 and the sleeve 6 are determined so that the positions of their tips 5a and 6a are nearly identical in the this condition.

Figure 3:
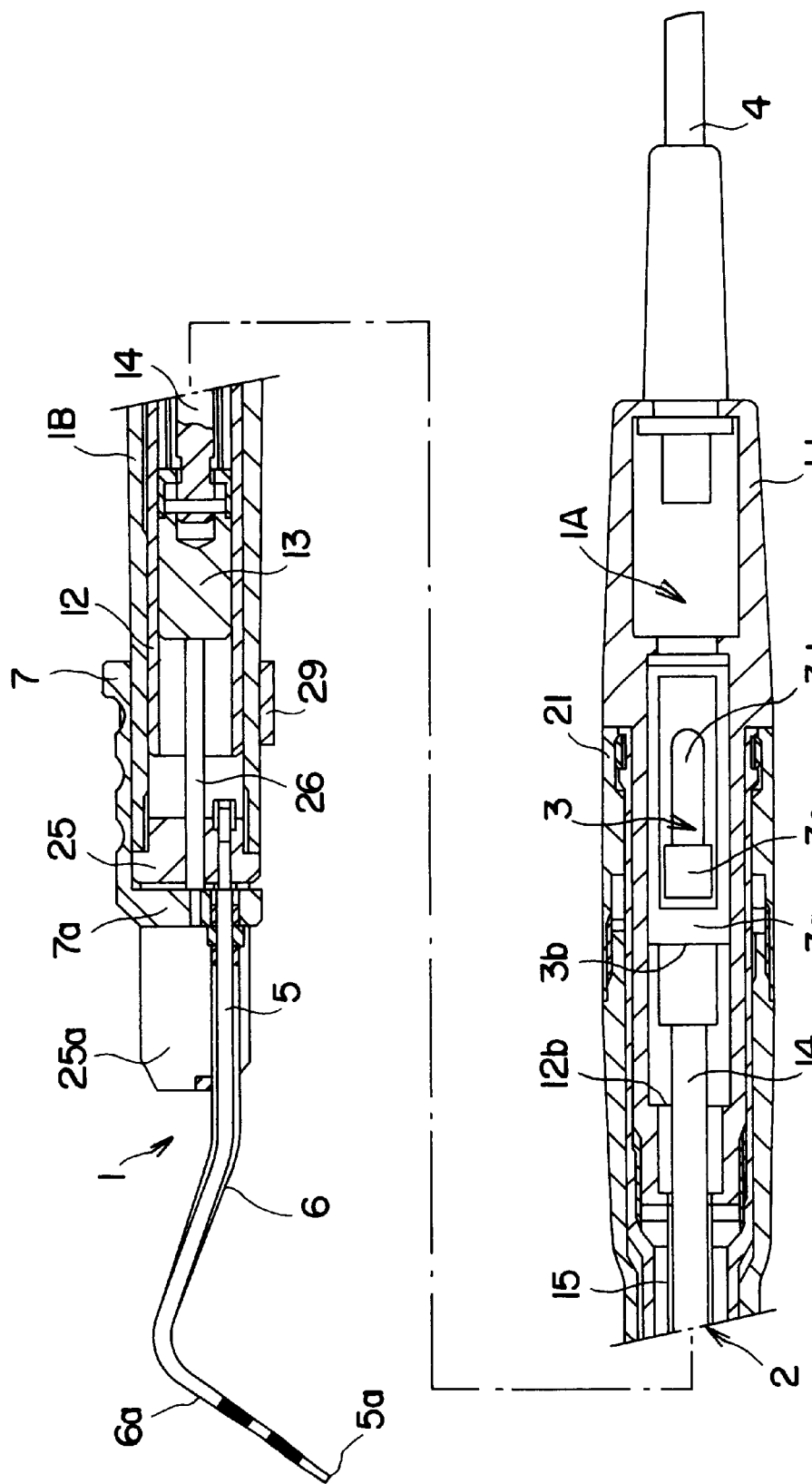
FIG. 3 is also an overall sectional view showing the handpiece.

Fig 3 shows a condition wherein the operation member 7 is moved backward by operating the operation member 7 or the ring-shaped operation portion 29 by an operator to the position wherein the front plate 7a makes contact with the front surface of the cap 25. By this operation, the sleeve 6 moves relatively to the probe 5, and the tip 6a of the sleeve 6 is positioned backward by the amount of the movement of the sleeve 6 from the tip 5a of the probe 5. This movement can be carried out smoothly, since the energizing force of the coil spring 15 is weak enough to ensure smooth operation, and the sleeve 6 is flexible. In accordance with this movement, the slider 13 is pushed by the push bar 26 and moved backward, and the traveling portion 3a of the sensor 3 connected via the connecting rod 14 is moved relatively to the stationary portion 3c. As a result, an interruption signal depending on the amount of movement is output from the phototransistor 3f of the stationary portion 3c.

Periodontal pocket measurement is conducted in accordance with the following procedure, for example. First, referring to FIG. 2, the position of the tip end 5a of the probe 5 is aligned with the position of the tip 6a of the sleeve 6 by operating the operation member 7. The positional relationship between the traveling portion 3a and the stationary portion 3c obtained at this time is stored and defined as the origin. In the condition shown in FIG. 3, wherein the operation member 7 is moved backward significantly, the tip 5a of the probe 5 is inserted into the bottom portion of a periodontal pocket of a patient, and the sleeve 6 is returned to the position wherein the tip 6a makes contact with the upper fringe of a gingiva. The positional difference between the tip 5a and the tip 6a obtained at this time, that is, the distance from the origin to the tip 6a corresponds to the depth of the periodontal pocket. Therefore, by detecting this distance, the depth of the periodontal pocket can be measured.

Figure 8:
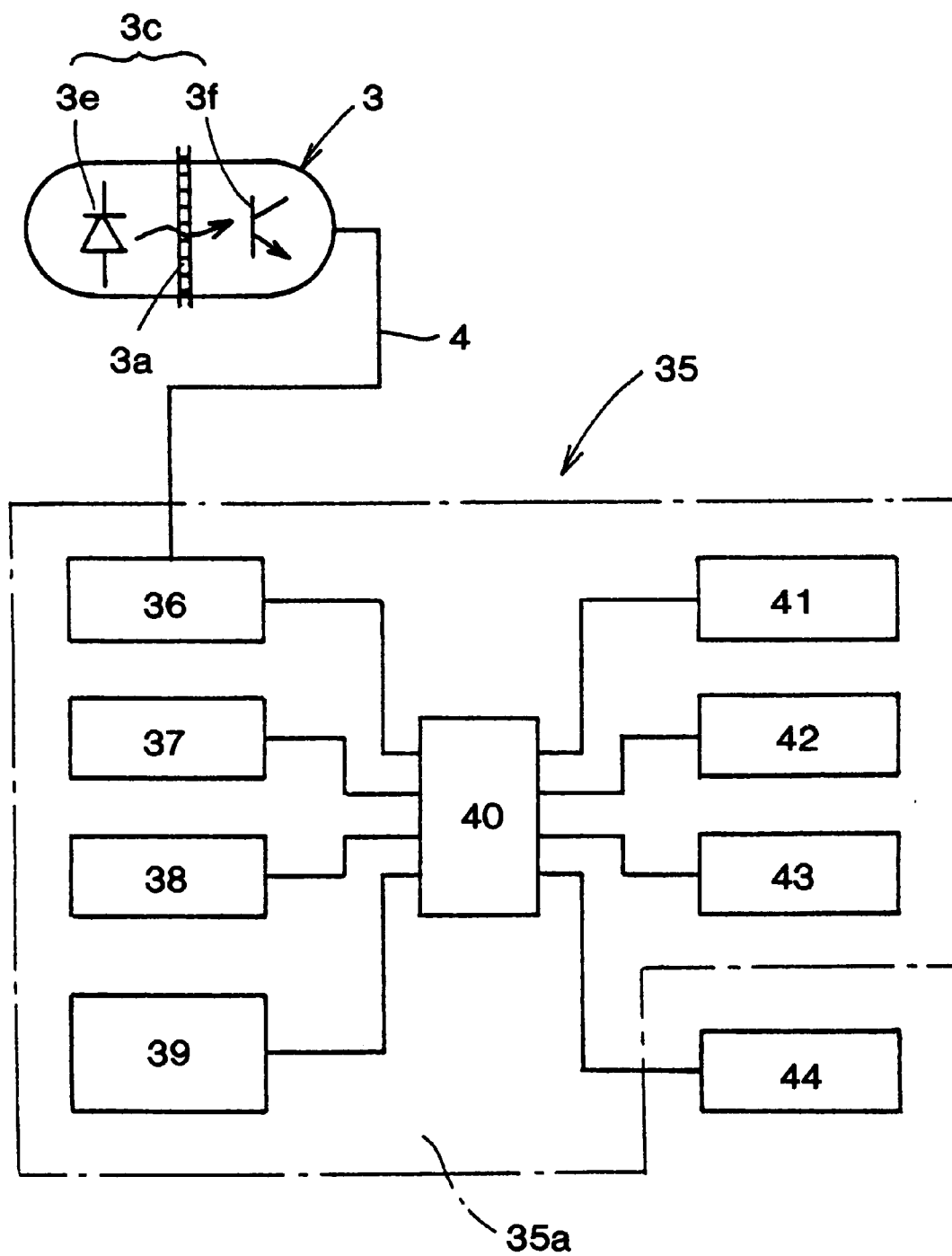
FIG. 8 is a block diagram showing the configuration of a measurement circuit.

A measurement circuit for detecting the movement distance of the traveling portion 3a by taking the above-mentioned operation procedure is described below referring to the block diagram shown in FIG. 8. Referring to FIG. 8, reference code 35 represents a measurement circuit, reference code 36 represents a waveform shaping circuit, reference code 37 represents a count change detection circuit, reference code 38 represents a counter circuit, reference code 39 represents an operation switch portion provided with a plurality of switches, and reference code 40 represents a control portion provided with a CPU. The setting of the above-mentioned origin is carried out by operating the predetermined switches of the operation switch portion 39 while the position of the tip 5a is aligned with the position of the tip 6a.

A signal for indicating the movement direction of the traveling portion 3a is also output from the sensor 3. When the sleeve 6 is moved backward, an interruption signal is sent from the sensor 3. This signal is shaped by the waveform shaping circuit 36. Change in count data is calculated in accordance with the movement direction by the count change detection circuit 37. The total count value is obtained by the counter circuit 38 and input to the control portion 40. When the tip 5a of the probe 5 is inserted into the bottom portion of the periodontal pocket, and the tip 6a of the sleeve 6 is returned to the position wherein the tip 6a of the sleeve 6 makes contact with the upper fringe of the gigiva, count data is changed by the interruption signal. From the change in the count data, the total count value is obtained and input to the control portion 40. Based on these values, the current position of the tip 6a of the sleeve 6, that is, the movement distance from the origin can be calculated, and the depth of the periodontal pocket can be obtained.

Although the alignment position of the tip 5a and the tip 6a is defined as the origin in the above-mentioned description, a desired position can be defined as the origin, and any difference can be corrected during measurement. For example, if the sleeve 6 is replaced with a new one, and its length is slightly different from that of the old one, the difference is corrected at the time of calculation, without resetting the origin.

Reference code 41 represents a display portion, reference code 42 represents a storage unit, reference code 43 represents a printer, and reference code 44 represents means for communication to other devices. In accordance with the operation of the operation switch portion 39, the above-mentioned measurement results are indicated, stored or printed out, or sent to other computers or the like so as to be used as diagnosis data.

Figure 9:
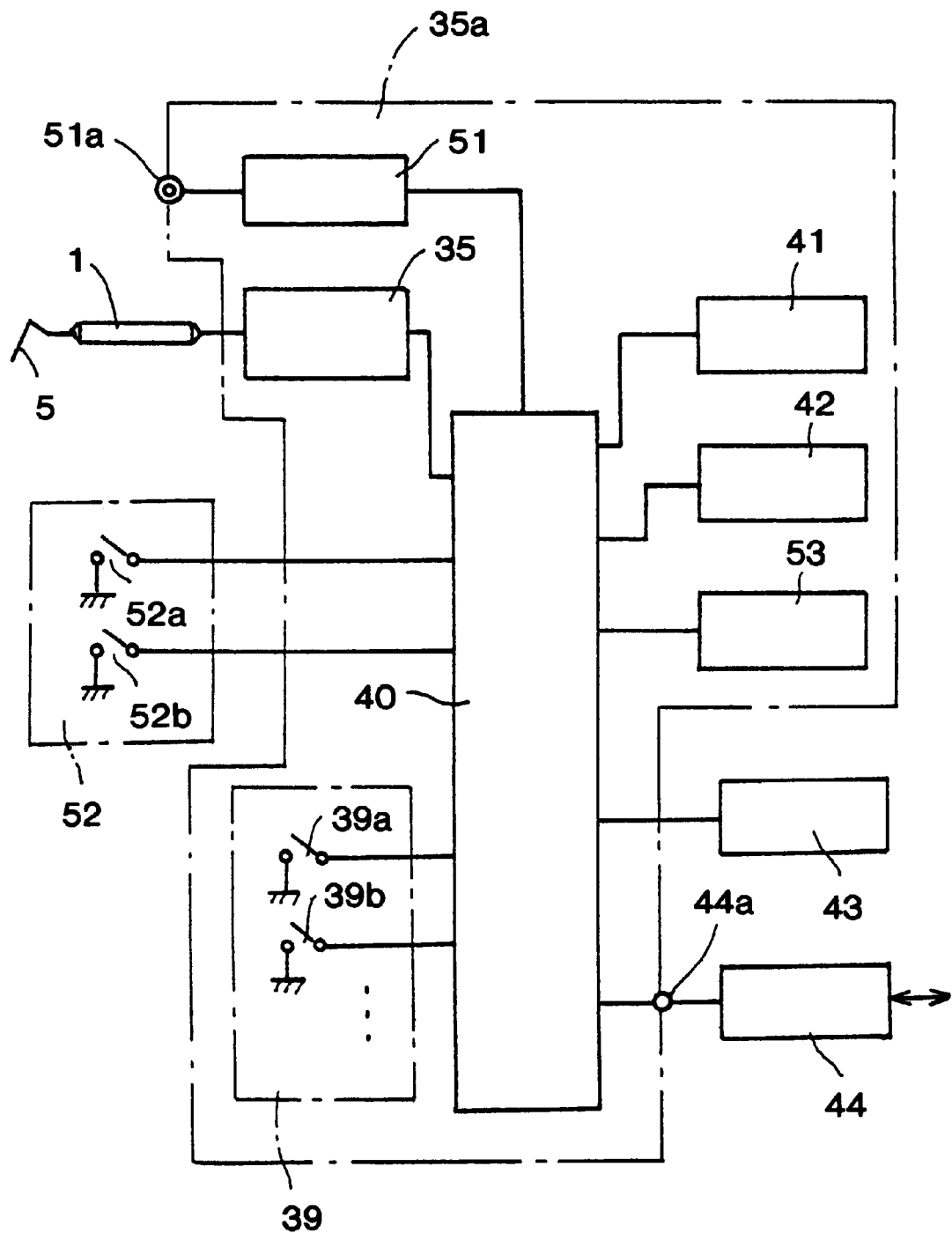
FIG. 9 is a block diagram showing the overall circuit configuration of a separately provided control unit.

Referring to FIG. 8, reference code 35a represents a main control unit, which comprises the circuits and devices enclosed by the chain line shown in FIG. 8 for example and is accommodated in a housing disposed separately from the main handpiece unit 1A. In this case, the power supply for activating the sensor 3 and the output signal from the sensor 3 are delivered or transmitted via the cord 4 for connecting the handpiece 1 to the main control unit 35a. The main control unit 35a may be an apparatus specially designed as a periodontal pocket measurement apparatus. However, since most circuits of the measurement circuit 35 can be used for measurements other than periodontal pocket measurement, the main control unit 35a may be a medical diagnostic apparatus having other functions and additionally provided with periodontal pocket measurement circuits, such as the counter circuit 38. An example of the main control unit 35a having such other functions is shown in FIG. 9 and detailed later.

In the above-mentioned system wherein the main handpiece unit 1A is connected to the main control unit 35a via the cord 4, the weight of the handpiece 1 can be reduced. However, the operability of the handpiece 1 is lowered because of the connection to the cord 4. The operability can therefore be improved when the handpiece 1 is made cordless by mounting a control PC board provided with at least circuits required for a function for setting the origin and a function for calculating the distance of movement of the tip 6a of the sleeve 6 with respect to the origin and for measuring the depth of the periodontal pocket and also by mounting a compact battery in the handpiece 1. In this case, it is possible to adopt appropriate means wherein obtained measurement result data having been stored temporarily is sent to a separately installed control unit when measurement is completed and the handpiece 1 is placed on a charger which is also used as a stand, for example.

The above-mentioned structure of the sensor 3 is just an example. It is possible to use an appropriate structure, for example, a digital type other than the above-mentioned type or an analog type such as a differential transformer type. In this case, the measurement circuit 35 should be a type corresponding to the type of the sensor.

Since the illustrated handpiece 1 has the above-mentioned structure, it can deliver various functions in practical use. First, since the sleeve 6 is formed of closely-wound thin metal wire, it is very flexible, and can move smoothly along the probe 5 during the operation of the operation member 7 even when the probe 5 is bent, whereby measurement can be conducted without disturbance. As the flexible sleeve 6, a pipe having a thin wall and made of fluororesin can also be used, for example.

In addition, since the cover member 1B is rotatable with respect to the base portion 11, it can be rotated appropriately together with the sleeve 6 and the probe 5 with respect to the main handpiece unit 1A, although the direction of the main handpiece unit 1A cannot be changed easily because of the connection to the cord 4. Furthermore, only the probe 5 can be rotated with respect to the cap 25 without rotating the cover member 1B together with the probe 5. Therefore, the probe 5 can be pointed in a desired direction depending on the direction of the tooth, and periodontal pocket measurement can be conducted easily. In this case, by mounting the removable ring-shaped operation portion 29 on the operation member 7, the operation member 7 is provided around the entire circumference of the cover member 1B regardless of the actual direction of the operation member 7, whereby its operability can be improved. On the other hand, the operation portion 29 can be removed when not necessary, thereby not causing any obstruction.

Moreover, the cap 25 is installed at the tip of the cover member 1B. Since the pipe-shaped member 12 of the main handpiece unit 1A and the slider 13 positioned at the tip thereof are completely covered with the cover member 1B and the cap 25, the pipe-shaped member 12 and the slider 13 do not make contact with the mouth of the patient during measurement, and the saliva, blood and the like of the patient do not enter the pipe-shaped member 12 and the slider 13. The cover member 1B, the operation member 7 and the cap 25 which may make contact with the mouth of the patient can be removed from the base portion 11 together with the probe 5 and the sleeve 6. Therefore, they can be easily subjected to sterilization by autoclave. This structure is thus significantly effective in obtaining a safe and sanitary apparatus. Besides, since the sleeve 6 is simply inserted into the sleeve catch 27, it can be replaced easily, and can be thrown away easily after use for each patient.

Since the slider 13 just pushes the push bar 26 and is not connected thereto, the slider 13 does not become obstructive, when the cover member 1B, the sleeve 6 and the probe 5 are rotated with respect to the main handpiece unit 1A as described above or when they are removed from the base portion 11. Additionally, since the limiting means 2a is formed of the front fringe 3b of the traveling portion 3a of the sensor 3 and the step portion 12b of the base portion 11. Therefore, even when the cover member 1B and the like are removed, such a problem as popping out of the slider 13 from the pipe-shaped member 12 toward the front end does not occur.

Next, the main control unit 35a shown in FIG. 9 is describe below. This example is structured so as to be used for examinations for mobility and plaque control, as well as periodontal pocket measurement. Therefore, the main control unit 35a comprises input means for inputting examination results of a plurality of such diagnosis items, display means for indicating the examination results and output means for outputting the examination results.

Figure 10:
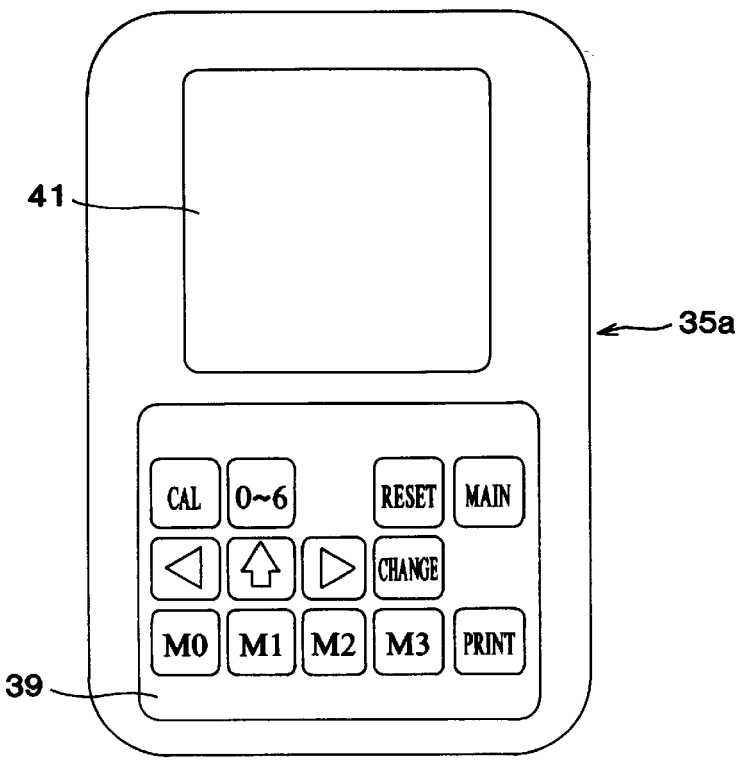
FIG. 10 is a front view showing the external appearance of the main unit of the control unit.

Referring to FIG. 9, reference code 51 represents an audio input circuit connected to a microphone 51a, reference code 52 represents a foot pedal provided with switches 52a and 52b, reference code 53 represents an audio output portion, and reference codes 39a, 39b, . . . represent a plurality of input switches of the operation switch portion 39. These devices and the above-mentioned circuits are connected to the control portion 40. FIG. 10 shows the external appearance of the main control unit 35a. On the front surface of the housing thereof, the display portion 41 formed of a liquid crystal panel for example and the operation switch portion 39 comprising a plurality of input keys are provided. The circuits enclosed by the chain lines in FIG. 9 are accommodated in the housing. In this example, the printer 43 is not provided for the main control unit 35a, but it is an external printer.

Reference code 44a represents a signal input/output terminal for signal transmission to other devices. The terminal is provided for data transmission and reception between the main control unit 35a and external devices, such as personal computers and host computers, via the communication means 44. The communication means 44 can perform two-way communication or at least either of transmission and reception, and can use various communication systems, such as wired and wireless systems, as necessary. The main portion, such as the transmission and reception circuits thereof, can be accommodated in the main control unit 35a. The printer 43 may also be connected via the communication means 44. In this case, a printer connected to an external device, such as a personal computer, can be used. The audio input circuit 51 is used to input tooth mobility data, for example. Measurement results obtained from the voice of the operator, that is, mobility data, is input to the control portion 40. As described above, the depth of the periodontal pocket can be detected as the positional difference between the tip of the probe 5 and the tip of the sleeve 6 obtained after the tip of the probe 5 of the handpiece 1 is inserted into the bottom portion of the periodontal pocket, and while this condition is maintained, the tip of the sleeve 6 covering the probe 5 is returned to the position wherein the tip of the sleeve 6 makes contact with the upper fringe of the gingiva. The result of the detection is input from the periodontal pocket depth measurement circuit 35 to the control portion 40. Furthermore, the foot pedal 52 is used to input plaque control examination results, for example. By operating either of the switches 52a and 52b, a signal indicating the presence or absence of plaque is input to the control portion 40. Instead of using the switches, appropriate switches selected from among the switches 39a, 39b, . . . of the operation switch portion 39, such as input keys M0, M1, M2 and M3, may be used.

Each examination result having been input as described above is indicated on the display portion 41 depending on the operation of the input switches 39a, 39b, . . . of the operation switch portion 39 or the like, stored in the storage unit 42, printed out by the printer 43, or output from the signal input/output terminal 44a to a personal computer or the like by the communication means 44, and then used as diagnosis data. The above-mentioned input operation is taken just as an example. By using the various input keys of the operation switch portion 39, a variety of input operations can be performed.

Indication by the display portion 41 and print output by the printer 43 are performed in accordance with predetermined formats. FIGS. 11A and 11B show examples of formats, which have been specified by the insurance system of Japan so as to be recorded on medical sheets, well known by dentists and required at the time of requesting insurance. FIG. 11A shows a format for precision oral examination, and FIG. 11B shows a format for basic oral examination. Since examination results are printed out in accordance with these formats, all the dentist has to do is to paste the printed formats on medical sheets, thus saving a lot of effort of manual writing. When this periodontal pocket measurement apparatus is used in counties outside Japan, control software capable of obtaining formats specified in each county can be used.

Figure 12:
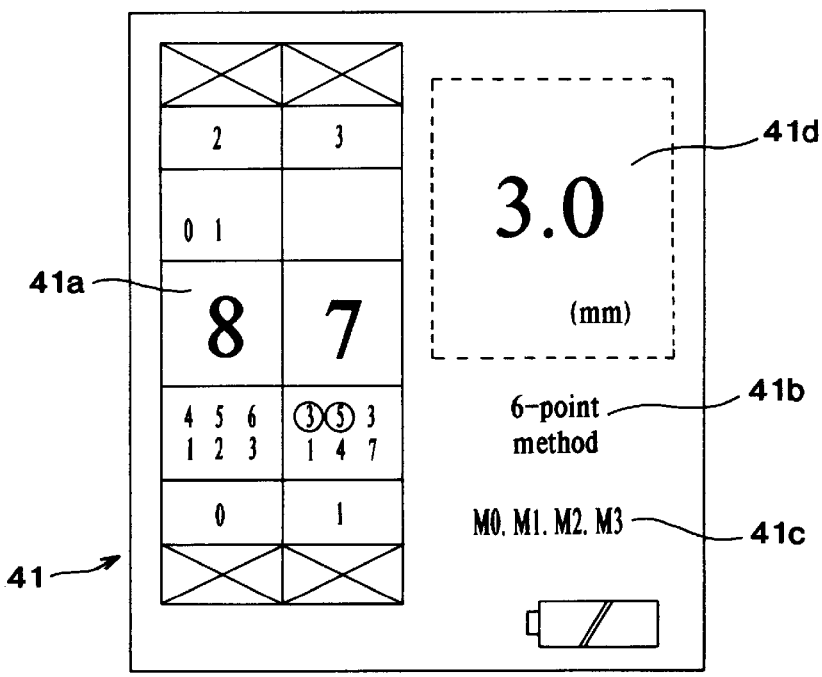
FIG. 12 shows an example of indication on the display portion of the control unit.

As shown in FIG. 12, the display portion 41 is provided with a region 41a for indicating a part of such a format as that described above, a region 41b for indicating an examination method, a region 41c for indicating a storage region, and a region 41d for indicating an examination result. FIG. 12 shows an example of indications by the display portion 41, which are obtained during measurement. Since the indications are performed in accordance with a predetermined format for a tooth to be measured, measurement can be conducted smoothly.

The storage unit 42 has a storage capacity capable of storing the measurement results for at least a plurality of patients, and is formed of a device capable of retaining storage data even after the power is turned off, such as an EEPROM. In this example, the storage unit 42 has storage regions for four patients. The storage regions to be used can be selected by operating the M0, M1, M2 and M3 keys of the operation switch portion 39. The audio output portion 53 is provided with an electronic buzzer, for example, and generates different signal sounds depending on the diagnosis item or the examination mode at the time of inputting examination results.

Figure 13:
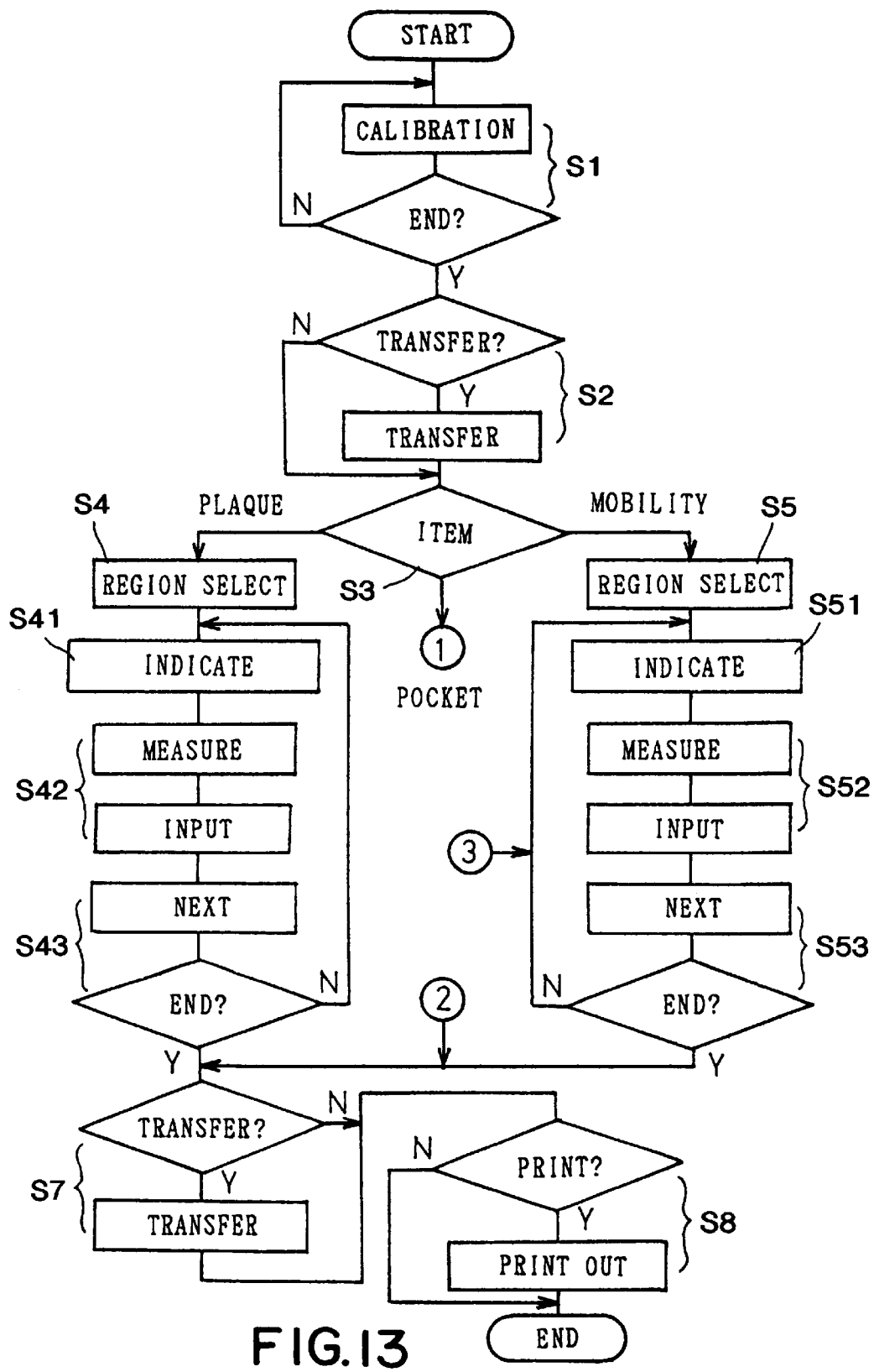
FIG. 13 is a flowchart showing a basic oral examination procedure for the control unit.
Figure 14:
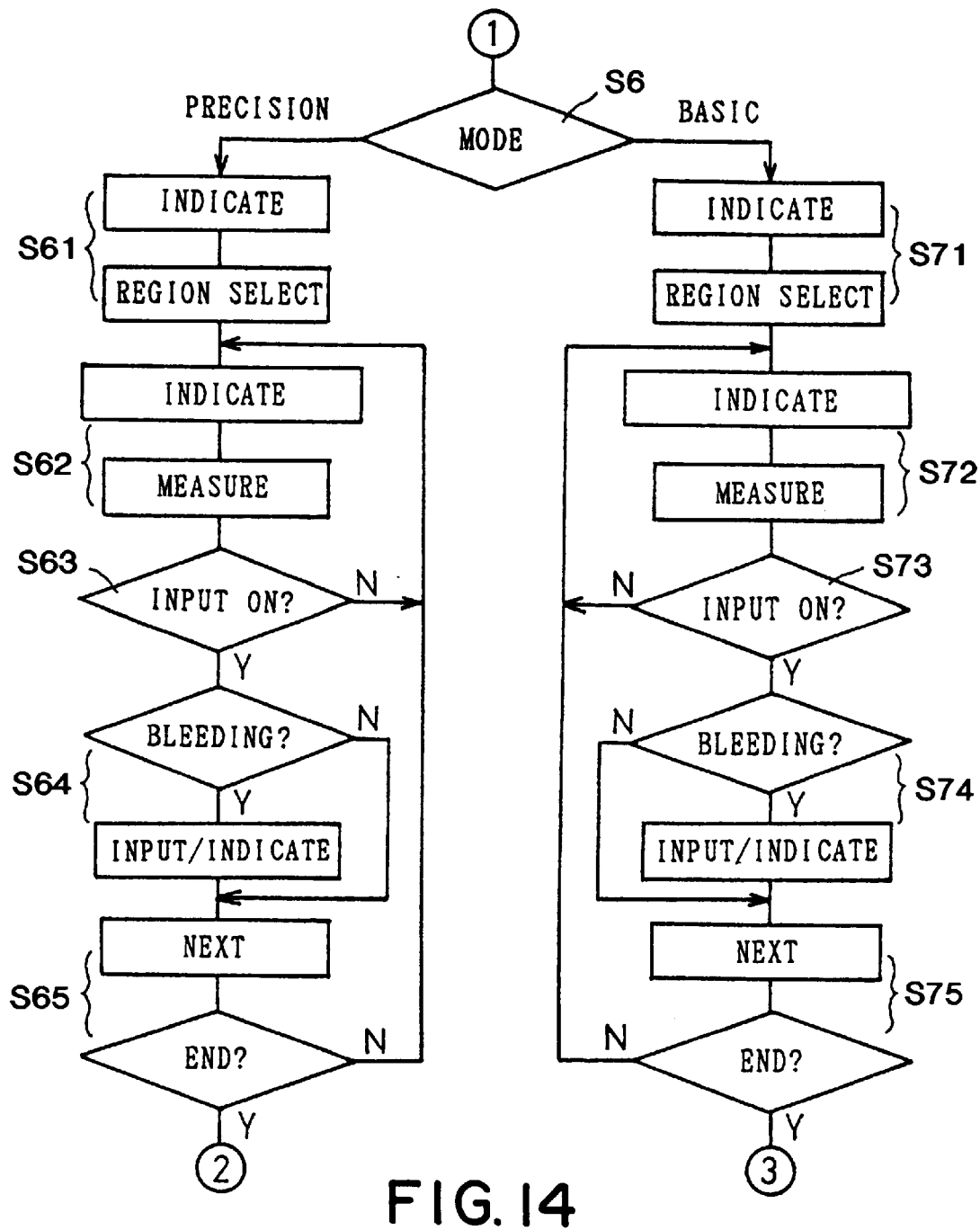
FIG. 14 is also a flowchart showing a basic oral examination procedure for the control unit.

Next, a basic examination procedure is described below referring to FIGS. 13 and 14. Keys and switches to be operated for the execution of the procedure are predetermined by a program or the like. The operations of the keys and switches described below are just examples and not limited to these examples. In other words, it is possible to use a different method. For example, necessary control can be performed by operating switches mounted on the handpiece 1.

Step S1 is a calibration step, wherein the zero adjustment of the above-mentioned handpiece 1 is conducted by using the CAL key shown in FIG. 10. After the calibration is completed, the CAL key is pressed again to proceed to the next step, S2. If no calibration is necessary because the handpiece 1 is a type requiring no calibration, for example, the procedure proceeds to step S2 immediately.

When the past examination results for a patient have already been stored in an external device, such as a personal computer, and the examination results for the patient are read and used for this diagnosis, whether the data is transferred or not is determined at step S2. If data transmission is necessary, the data is transferred to this apparatus by the communication means 44, and the procedure proceeds to step S3. If not necessary, the procedure proceeds to step S3 immediately.

Step S3 is used to select one of diagnosis items, that is, one of examination modes: plaque control, mobility and depth of periodontal pocket. This selection is carried out by operating the selection switch shown in FIG. 10. The procedure then proceeds to step S4, S5 or S6 depending on the result of the selection.

As shown in FIG. 12, the region 41a of the display portion 41 indicates a portion of the precision oral examination format, that is, the tooth to be examined currently and the tooth to be examined next. Initially, the indication in the region 41a appears with no data, and the indication portions for a selected item and a measurement position corresponding to the item flash. As the measurement proceeds, the flashing indication is changed to the steady lighting indication of results in sequence. When the measurement of the tooth to be measured currently is completed, the indication portions for the item and a measurement position corresponding to the item for the next tooth begin to flash automatically. FIG. 12 shows a condition where examination is shifted from the examination of teeth of the lower jaw, and the central periodontal pocket on the lingual side of the first tooth of the upper jaw, that is, the eighth tooth at the upper right area of the upper jaw is being measured. The indication for this measurement position flashes, and the indications for the measurement positions yet to be measured and the seventh tooth of the upper jaw to be examined next have no data.

The procedure proceeds to step S4 when plaque control examination is selected. When one of the usage regions of the storage unit 42 is selected by using the M0, M1, M2 and M3 input keys of the operation switch portion 39, the indication corresponding to the selected usage region of the region 41c flashes. The procedure proceeds to step S41, and plaque input ready indication appears. At the next step, S42, the dentist carries out plaque measurement by using a desired method. For example, by operating the foot pedal 52, the result of the measurement is input to the control portion 40. After this, the procedure proceeds to step S43, the plaque indication portion for the measurement position lights steadily in the region 41a to indicate the input results, and the indication portion for the next measurement position flashes.

As described above, the indication portion for the measurement position whose data is input next flashes, and the tooth number of the tooth to be examined is indicated. Therefore, the dentist can easily confirm which portion of which tooth is currently subjected to which examination. The dentist can thus perform the next operation properly. In addition, since signal sounds are delivered from the audio output portion 53 depending on the diagnosis item and the examination mode at the time of input of examination results, frequency of viewing the display portion 41 can be reduced, and operation speed can be increased. In this way, the indication of teeth to be examined is shifted automatically in the predetermined sequence, and the procedure from step S41 to step S43 is repeated. When the examination of all the teeth is completed, the procedure proceeds to step S7. The input keys of the operation switch portion 39 can also be used to change or select teeth to be examined.

Furthermore, when the mobility examination has been selected, and the procedure have proceeded to step S5, a usage region of the storage unit 42 is selected just as in the case of step S4, and mobility input ready indication appears at step S51. At step S52, the dentist measures mobility by using a desired method. When the dentist speaks into the microphone 51a to input the result, the result is input to the control portion 40. The procedure then proceeds to step S53. The result is indicated in the region 41a by lighting the mobility indication portion corresponding to the measurement position whose data has been input, and the indication portion for the next measurement position flashes. The procedure from step S51 to step S53 is then repeated. After the examination of all the teeth is completed in the predetermined sequence, the procedure proceeds to step S7.

When the periodontal pocket examination is selected, and the procedure proceeds to step S6, the precision oral examination or the basic oral examination is selected by the operation of the input keys of the operation switch 39, for example. When the precision oral examination is selected, the procedure proceeds to step S61, and precision oral examination indication appears. When a usage region of the storage unit 42 is selected just as in the case of step S4, pocket measurement ready indication flashes at step S62. The measurement is conducted by using the handpiece 1 at this step. When a signal for inputting the measurement result for the measurement position is input at step S63 by the operation of the foot pedal 52, for example, the measurement result is input from the measurement circuit 35 to the control portion 40. In the region 41a, the periodontal pocket depth indication portion corresponding to the measurement position is changed to the indication of the measurement result, and lights steadily to indicate the depth value of the periodontal pocket.

When bleeding is recognized, the bleeding condition is input at step S64, and bleeding input indication appears. The procedure proceeds to step S65, and the indication portion for the next measurement position flashes. As shown for the seventh tooth of the lower jaw in FIG. 12, the bleeding input indication is performed by circling the number of the measurement value of the periodontal pocket, for example. In the case of nonbleeding, when the nonbleeding condition is input, the procedure proceeds to step S65 immediately, and the indication portion for the next measurement position flashes. The procedure from step S62 to step S65 is repeated until the examination of all the teeth is completed in the predetermined sequence. After the examination, the procedure proceeds to step S7.

On the other hand, when the basic oral examination mode is selected at step S6, the procedure proceeds to step S71, and the indication at the display portion 41 changes to the basic oral examination format shown in FIG. 11B. The indication portion for the tooth number for the first examination appears with no data, and the indication portion for a selected item flashes. When a usage region of the storage unit 42 is selected just as in the case of step S4, the procedure proceeds to step S72, pocket measurement ready indication appears, and measurement by using the handpiece 1 is conducted. When a signal for inputting the measurement result at the measurement position is input at step S73, the indication portion corresponding to the measurement position in the region 41a changes to the indication of the measurement result, and lights to indicate the depth value of the periodontal pocket.

Furthermore, the input and indication regarding bleeding at the next step, S74, is similar to those at step S64. After the step, the procedure proceeds to step S75, and the indication portion for the next measurement position flashes. The procedure from step S72 to step S75 is repeated until the periodontal pocket depth examination of all the teeth is completed in the predetermined sequence. In the case of the basic oral examination, both the periodontal pocket examination and the mobility examination are required. Therefore, after the above-mentioned periodontal pocket examination, the procedure proceeds to step S51 automatically. The procedure from step S51 to step S53 is repeated so as to perform the mobility examination for all the teeth. After the examination, the procedure proceeds to step S7.

Step S7 determines whether or not the examination results of this time are transferred to and stored in an external storage unit, such as a storage unit in a personal computer. If necessary, data is transferred by the communication means 44 and stored. If not necessary, the procedure proceeds to step S8 immediately.

Step S8 checks whether the print key of the operation switch portion 39 has been operated or not. If operated, all the above-mentioned examination results are printed out in the predetermined format, and the series of operations come to an end. If not operated, the procedure ends immediately. When an external printer is used as the printer 43, the examination result data is transferred to the external printer by the communication means 44 and then printed out.

Since the storage unit 42 of the present apparatus can store examination results for four patients, examination can be continued for four patients. Therefore, instead of ending the procedure at step S8 as described above, the procedure may return to step S3 so that examination for the next patient can be continued. In this case, key M0 of the operation switch portion 39 is operated first and the corresponding usage region is selected so that after this the usage regions corresponding to M1, M2 and M3 can be selected in sequence automatically.

The data stored in the storage unit 42 can be retained even when the storage unit 42 is turned off, unless operation for data deletion is carried out. In addition, since the data can be transferred to and received from other devices, such as personal computers and host computers, by the communication means 44, it is possible to store the examination results for many patients in a large storage unit. Accordingly, at a later date, it is easily possible to read necessary data from the storage unit 42 or an external storage unit, to indicate the data on the display portion 41, and to print out the data. For example, after the examination result data of a specific patient has been stored in the storage unit 42 or an external storage unit for several months, it is possible to read the data at the time of diagnosis, and to perform data rewriting and comparison after periodontal pocket measurement conducted only at pathologically changed portions. Since various data processing can be carried out in this way, the apparatus for the present embodiment can flexibly perform various processing required clinically.

As described above, a single unit of the apparatus of the present embodiment can process all examination result data of various periodontal diseases, such as those related to periodontal pocket, tooth mobility and plaque control. Since input can be accomplished by switch operation or the like, manual writing is not necessary. In addition, these examination results can be output in predetermined formats, and the printed results in table forms can be pasted on medical sheets. Therefore, effort and time for manual writing can be saved, and clerical work incident to diagnosis can be rationalized.

Furthermore, since a diagnosis item, a tooth being examined and the examination results of the tooth are indicated at the display portion 41 in predetermined formats, the dentist can easily confirm which portion of which tooth is currently subjected to which examination. Consequently, diagnosis can be conducted easily, and operation errors can be prevented.

What is claimed is:

1. A periodontal pocket measurement apparatus comprising a main handpiece unit provided with a cylindrical cover member covering a front end portion of said main handpiece unit, an operation member slidably mounted at a front end of said cylindrical cover member which is slidable in a longitudinal direction of said cylindrical cover member, a flexible sleeve attached to said operation member and projecting from the front end of said cylindrical cover member, a probe attached to said cylindrical cover member, said probe passing through said sleeve and being exposable at its tip from a tip of said sleeve, and an energizing means for pushing a movable portion comprising said operation member and said sleeve toward the front end of said cylindrical cover; and wherein said sleeve is formed of closely wound thin metal wire;

said energizing means has a pushing member; and said movable portion is energized toward the front end of said cylindrical cover member by contacting said pushing member with said movable portion.

2. A periodontal pocket measurement apparatus according to claim 1, wherein limiting means is provided to stop the movement of said movable portion at the position where the tip of said sleeve aligns or nearly aligns with the tip of said probe.

3. A periodontal pocket measurement apparatus according to claim 2, wherein said limiting means is provided in said main handpiece unit and structured so as to limit the movement of said pushing member in the front end direction at a predetermined position.

4. A periodontal pocket measurement apparatus according to claim 1, wherein the energizing force of said energizing means is generated by a compressed coil spring.

5. A periodontal pocket measurement apparatus according to claim 1, said apparatus further comprising a stationary portion provided in said main handpiece unit, a traveling portion connected to said pushing member of said energizing means and moving together with said pushing member, and a sensor for detecting the displacement of said traveling portion with respect to said stationary portion and for outputting a detection signal corresponding to the movement distance of said sleeve.

6. A periodontal pocket measurement apparatus according to claim 5, wherein depending on the output from said sensor said main handpiece unit is provided with a measurement circuit having at least a function capable of setting the alignment position of the tip of said sleeve and the tip of said probe or a desired position as the origin, and a function capable of calculating the movement distance of the tip of said sleeve from the origin.

7. A periodontal pocket measurement apparatus according to claim 5, wherein depending on the output from said sensor a control unit provided separately from said main handpiece unit is provided with a measurement circuit having at least a function capable of setting the alignment position of the tip of said sleeve and the tip of said probe or a desired position as the origin, and a function capable of calculating the movement distance of the tip of said sleeve from the origin.

8. A periodontal pocket measurement apparatus according to claim 7, wherein said control unit comprises output means for outputting calculation results obtained by said measurement circuit in accordance with a predetermined format indicating the tooth numbers of teeth having been measured and the depth of a periodontal pocket at each measurement position.

9. A periodontal pocket measurement apparatus according to claim 8, wherein said control unit comprises storage means capable of storing the examination results for a plurality of patients.

10. A periodontal pocket measurement apparatus according to claim 9, wherein said control unit comprises communication means capable of at least transmitting or receiving examination results between said control unit and external devices.

11. A periodontal pocket measurement apparatus according to claim 8, 9 or 10, wherein said output means comprises display means for indicating a tooth being examined and the depth of a periodontal pocket at each measurement position of the tooth in accordance with a predetermined format at the time of input of examination results.

12. A periodontal pocket measurement apparatus according to claim 11, wherein said control unit comprises selection means for selecting a tooth to be examined, and is structured so that the number of the selected tooth can be indicated on said display means.

13. A periodontal display measurement apparatus according to claim 11, wherein said output means has a function to print out all examination results in accordance with a predetermined format.

14. A periodontal pocket measurement apparatus according to claim 11, wherein said control unit is structured so as to select either of precision oral examination and basic oral examination modes.

15. A periodontal pocket measurement apparatus according to claim 11, wherein said output means is structured so as to generate signal sounds at the time of inputting examination results.

16. A periodontal pocket measurement apparatus according to claim 1, wherein said cover member is structured so as to be rotatable together with said sleeve and said probe with respect to the longitudinal axis of said main handpiece unit.

17. A periodontal pocket measurement apparatus according to claim 1, wherein said cover member is structured so as to be removable from said main handpiece unit together with said sleeve and said probe.

18. A periodontal pocket measurement apparatus according to claim 17, wherein said cover member is structured so as to be rotatable together with said sleeve and said probe with respect to the longitudinal axis of said main handpiece unit.

19. A periodontal pocket measurement apparatus according to claim 1, wherein said probe is structured so as to be rotatable with respect to the longitudinal axis of said cover member.

20. A periodontal pocket measurement apparatus according to claim 1, wherein said sleeve is structured so as to be removable from said operation member.

21. A periodontal pocket measurement apparatus according to claim 20, wherein a wire-winding diameter at the tip of said sleeve is made smaller in accordance with a shape of said probe.

22. A periodontal pocket measurement apparatus according to claim 1, wherein at least said cover member, probe and operation member are made of heat-resistant materials.

23. A periodontal pocket measurement apparatus according to claim 1, wherein said operation member comprises a ring-shaped operation portion enclosing the circumference of said cover member.

24. A periodontal pocket measurement apparatus according to claim 23, wherein said ring-shaped operation portion is removable.

* * * * *